United States Patent
Watanabe et al.

(10) Patent No.: US 9,404,865 B2
(45) Date of Patent: Aug. 2, 2016

(54) DEVELOPED-COLOR MEASUREMENT APPARATUS AND METHOD

(71) Applicant: FUJIFILM Corporation, Tokyo (JP)

(72) Inventors: Koji Watanabe, Ashigarakami-gun (JP); Tomonori Nishio, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/592,363

(22) Filed: Jan. 8, 2015

(65) Prior Publication Data

US 2015/0125362 A1 May 7, 2015

Related U.S. Application Data

(63) Continuation of application No. PCT/JP2013/003921, filed on Jun. 24, 2013.

(30) Foreign Application Priority Data

Jul. 9, 2012 (JP) ................................. 2012-153283

(51) Int. Cl.
*G01N 21/64* (2006.01)
*G01N 33/543* (2006.01)

(52) U.S. Cl.
CPC .......... *G01N 21/6428* (2013.01); *G01N 33/543* (2013.01)

(58) Field of Classification Search
CPC .............. G01N 21/78; G01N 21/8483; G01N 21/6428; G01N 33/543
USPC ......................... 435/7.9; 422/82.05
See application file for complete search history.

(56) References Cited

U.S. PATENT DOCUMENTS

| | | | |
|---|---|---|---|
| 7,223,367 B1* | 5/2007 | Vossmeyer | G01N 15/0227 422/82.05 |
| 2009/0093968 A1* | 4/2009 | Kawamata et al. | 702/19 |
| 2010/0161243 A1* | 6/2010 | Nagai | G01N 35/00663 702/25 |
| 2011/0053181 A1 | 3/2011 | Hazama et al. | |
| 2011/0104810 A1* | 5/2011 | Shiba et al. | 436/50 |
| 2011/0129816 A1 | 6/2011 | Muraguchi et al. | |
| 2011/0136142 A1 | 6/2011 | Oyamada et al. | |

(Continued)

FOREIGN PATENT DOCUMENTS

| | | |
|---|---|---|
| JP | 2001-59844 A | 3/2001 |
| JP | 2009-216695 A | 9/2009 |
| JP | 2010-14620 A | 1/2010 |

(Continued)

OTHER PUBLICATIONS

International Search Report, issued in PCT/JP2013/003921, dated Aug. 13, 2013.

(Continued)

*Primary Examiner* — Jill Warden
*Assistant Examiner* — Jacqueline Brazin
(74) *Attorney, Agent, or Firm* — Birch, Stewart, Kolasch & Birch, LLP (57) ABSTRACT

Judgment as to whether an analyte is present is performed before a washing step in which a washing liquid for washing a test area and the vicinity of the test area is supplied to a test strip. If the analyte is detected, the judgment ends, but if the analyte is not detected, judgment is performed again after the test area and the vicinity of the test area are washed.

6 Claims, 5 Drawing Sheets

(56) References Cited

U.S. PATENT DOCUMENTS

2011/0244591 A1* 10/2011 Sendai .................. G01N 21/78
    436/164
2012/0094307 A1* 4/2012 Tajima ............. G01N 33/543
    435/7.4

FOREIGN PATENT DOCUMENTS

| JP | 2011-52971 A | 3/2011 |
| JP | 2011-117906 A | 6/2011 |
| JP | 2011-252819 A | 12/2011 |
| WO | WO 2007/007849 A1 | 1/2007 |
| WO | WO 2009/148150 A1 | 12/2009 |
| WO | WO 2010/122990 A1 | 10/2010 |

OTHER PUBLICATIONS

Written Opinion of the International Searching Authority, issued in PCT/JP2013/003921, dated Aug. 13, 2013.

Japanese Office Action dated Dec. 8, 2015 issued in corresponding Japanese Patent Application No. 2014-524624 with a partial English translation.

* cited by examiner

DEVELOPED-COLOR MEASUREMENT APPARATUS AND METHOD

CROSS-REFERENCE TO RELATED APPLICATIONS

This application is a Continuation of PCT International Application No. PCT/JP2013/003921 filed on Jun. 24, 2013, which claims priority under 35 U.S.C. §119(a) to Japanese Patent Application No. 2012-153283 filed on Jul. 9, 2012. Each of the above applications is hereby expressly incorporated by reference, in its entirety, into the present application.

BACKGROUND OF THE INVENTION

1. Field of the Invention

The present invention relates to a developed-color measurement apparatus and method for performing quantitative or qualitative measurement about an analyte in a sample solution.

2. Description of the Related Art

Many devices that easily and quickly perform a test about an analyte have been developed in recent years. In the devices, a sample solution that may contain the analyte is supplied to a test strip, and test about the analyte is performed by immunochromatography to test in-vitro diagnostic reagents, toxic substances and the like (please refer, for example, to International Patent Publication No. 2007/007849 (Patent Document 1)). For example, a sample solution is obtained by mixing a sample in which an analyte (for example, an antigen) may be present to a labeled second antibody that specifically binds to the analyte, and the sample solution is developed on an insoluble carrier made of porous material, and on which a first antibody that specifically binds to the analyte is immobilized in a specific area (test line). Then, an antigen-antibody reaction between the analyte and the first antibody and an antigen-antibody reaction between the analyte and the second antibody occur on the test line, and the test line becomes a color developed state as the test line is colored or a change in color occurs on the test line. Quantitative measurement as to whether the analyte is present in the sample solution or qualitative measurement (negative/positive) is performed by observing the color developed state of this test line.

Further, a method has been proposed to improve the reliability of measurement by developing a washing liquid on a test line and the vicinity of the test line (background), thereby removing labels in the background. Accordingly, a noise component is reduced, and an S/N ratio is improved (please refer, for example, to Japanese Unexamined Patent Publication No. 2009-216695 (Patent Document 2)).

SUMMARY OF THE INVENTION

In the method for improving the signal-to-noise ratio by developing the washing liquid, the reliability of measurement may improve. However, since a washing step is required before each measurement, a long time is needed for measurement.

In view of the foregoing circumstances, it is an object of the present invention to provide a developed-color measurement apparatus and method that can achieve both the reliability of measurement and reduction in time for measurement.

A developed-color measurement apparatus of the present invention includes a light source that outputs excitation light that excites a fluorescent label, a judgment means that detects a fluorescence emission state of a fluorescent label captured, through an analyte, in a test area of a test strip including an insoluble carrier in which the test area that reacts to the analyte contained in a sample solution is formed, while the excitation light is output to the test area, and performs, based on a result of the detection, judgment as to whether the analyte is present in the sample solution, a washing liquid supply means that supplies a washing liquid for washing the test area and the vicinity of the test area to the test strip, and a control means that controls the judgment means and the washing liquid supply means in such a manner that the judgment as to whether the analyte is present in the sample solution is performed after the sample solution has been supplied to the test strip but before the test area and the vicinity of the test area are washed, and if the analyte is detected, the judgment ends, but if the analyte is not detected, the judgment is performed again after the test area and the vicinity of the test area are washed.

In the developed-color measurement apparatus of the present invention, it is desirable that the judgment means detects a fluorescence emission state of the test area and a fluorescence emission state of the vicinity of the test area, and judges that the analyte is present in the test strip if a difference between a detection value in the test area and a detection value in the vicinity of the test area exceeds a predetermined threshold. In that case, it is desirable that a threshold in the judgment after washing is set greater than a threshold in the judgment before washing.

Further, it is desirable that the fluorescent label is a semiconductor nanoparticle or nanoparticles.

A developed-color measurement method of the present invention is a developed-color measurement method in a developed-color measurement apparatus including a light source that outputs excitation light that excites a fluorescent label, a judgment means that detects a fluorescence emission state of a fluorescent label captured, through an analyte, in a test area of a test strip including an insoluble carrier in which the test area that reacts to the analyte contained in a sample solution is formed, while the excitation light is output to the test area, and performs, based on a result of the detection, judgment as to whether the analyte is present in the sample solution, and a washing liquid supply means that supplies a washing liquid for washing the test area and the vicinity of the test area to the test strip. Further, the judgment as to whether the analyte is present in the sample solution is performed after the sample solution has been supplied to the test strip but before the test area and the vicinity of the test area are washed, and if the analyte is detected, the judgment ends, but if the analyte is not detected, the judgment is performed again after the test area and the vicinity of the test area are washed.

In the developed-color measurement method of the present invention, when the judgment means detects a fluorescence emission state of the test area and a fluorescence emission state of the vicinity of the test area, and judges that the analyte is present in the test strip if a difference between a detection value in the test area and a detection value in the vicinity of the test area exceeds a predetermined threshold, it is desirable that a threshold in the judgment after washing is set greater than a threshold in the judgment before washing.

Here, the test strip may be any kind as long as the test area becomes a fluorescence emission state when the analyte is present. For example, the test strip may use chromatography, particularly, an immunochromatography method, in which immunoassay utilizing an antigen-antibody reaction is applied to chromatography. Further, the pattern form of the test area is not limited. For example, the test area may be formed in a line shape, or the test area may have a predetermined pattern.

According to the developed-color measurement apparatus and method of the present invention, judgment as to whether the analyte is present is performed before the washing step in which a washing liquid for washing the test area and the vicinity of the test area is supplied to the test strip. If the analyte is detected, the judgment ends, but if the analyte is not detected, the judgment is performed again after the test area and the vicinity of the test area are washed. In this manner, washing is performed only when the analyte is not detected. Therefore, it is possible to achieve both the reliability of measurement and reduction in time for measurement.

Further, when the judgment means detects a fluorescence emission state of the test area and a fluorescence emission state of the vicinity of the test area, and judges that the analyte is present in the test strip if a difference between a detection value in the test area and a detection value in the vicinity of the test area exceeds a predetermined threshold, the possibility of erroneous detection is lower as a greater value is set as the threshold. Therefore, the accuracy of detection is improved. At the same time, the possibility of missing detection becomes higher. However, in the developed-color measurement apparatus and method of the present invention, since an S/N ratio is improved by washing, it is possible to improve the accuracy of detection in the judgment processing performed after washing by setting a greater threshold for the judgment processing after washing than the threshold for the judgment processing before washing.

When the fluorescent label is a semiconductor nanoparticle or nanoparticles, high-intensity fluorescence emission is obtainable. Further, when the fluorescent label is the semiconductor nanoparticle or nanoparticles, it is possible to separate the wavelength of excitation light and the wavelength of fluorescence from each other by a great difference. In such structure, it is possible to easily distinguish fluorescence emission and excitation light from each other. Therefore, it is possible to further improve the accuracy of detection.

DESCRIPTION OF THE PREFERRED EMBODIMENTS

Figure 1:
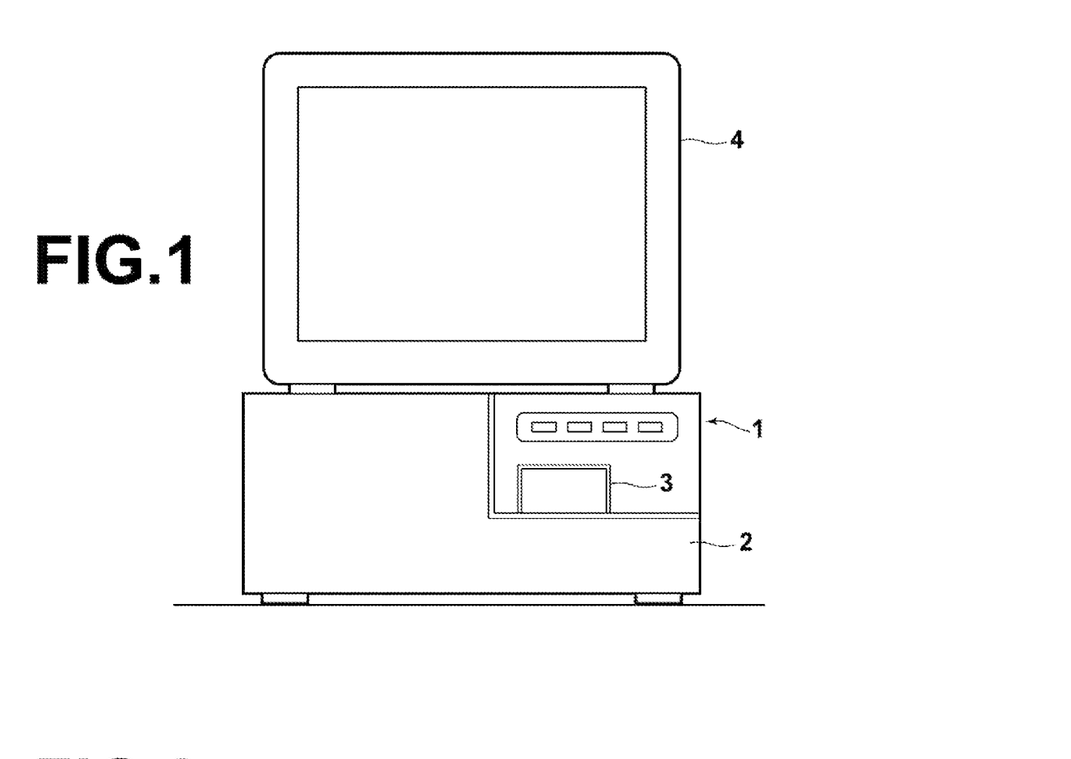
FIG. 1 is a schematic diagram illustrating a developed-color measurement apparatus according to a desirable embodiment of the present invention.
Figure 2:
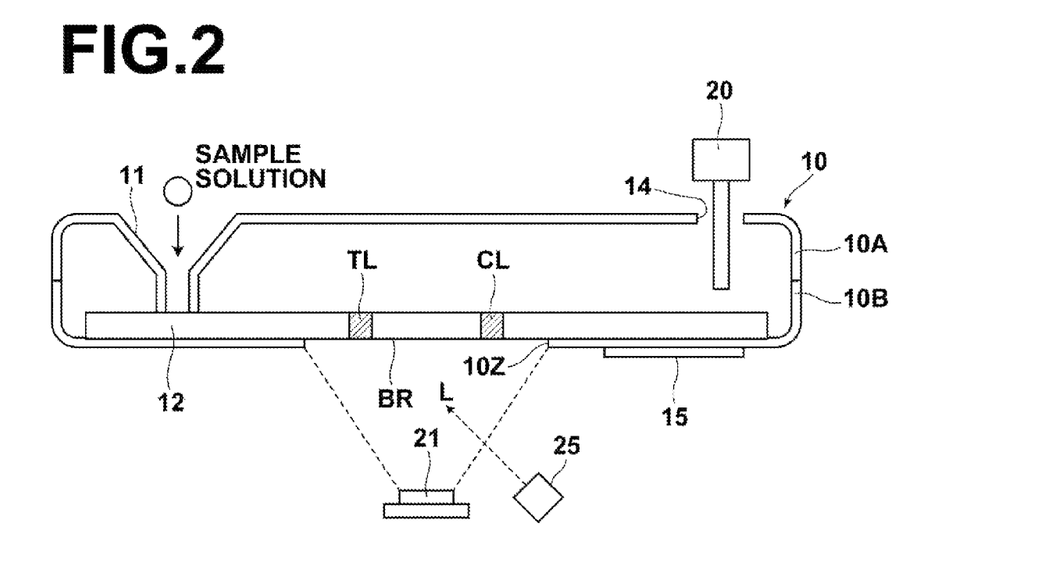
FIG. 2 is a schematic diagram illustrating an example of a test strip used in the developed-color measurement apparatus of the present invention.
Figure 3:
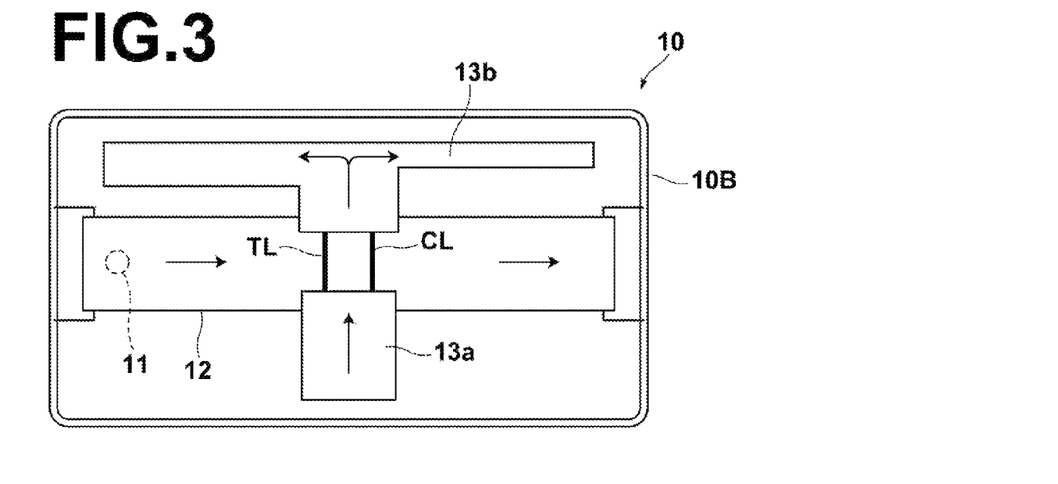
FIG. 3 is a schematic diagram illustrating an example of a test strip used in the developed-color measurement apparatus of the present invention.
Figure 4:
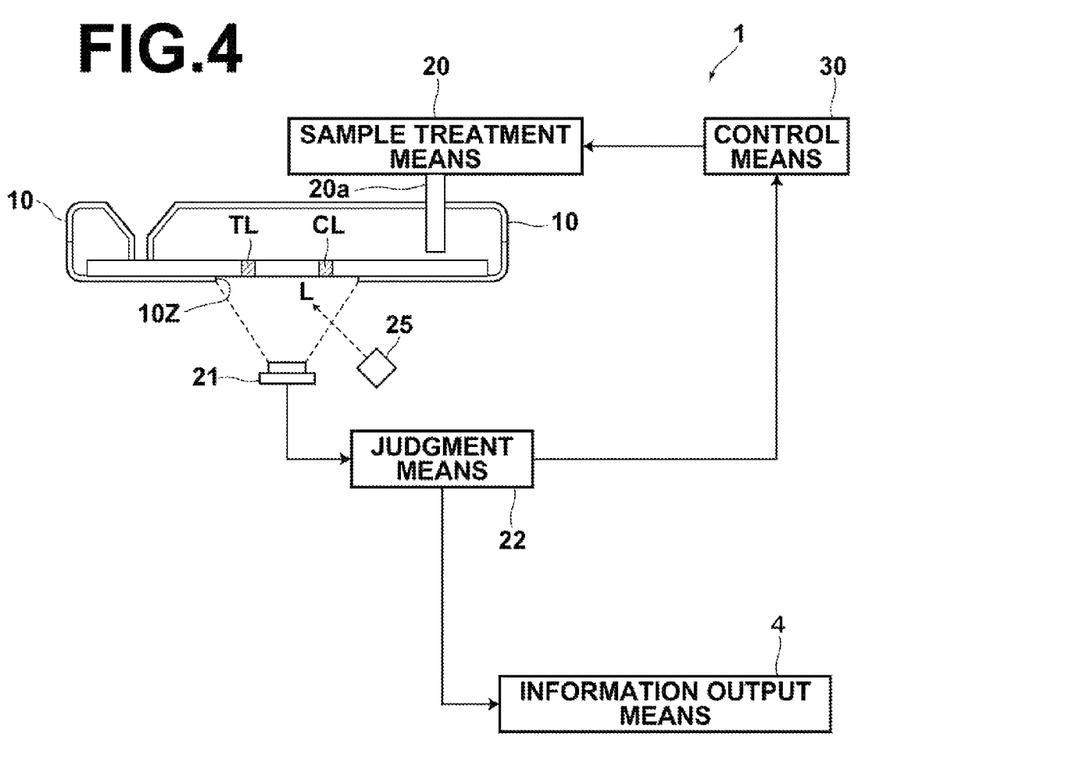
FIG. 4 is a block diagram illustrating a developed-color measurement apparatus according to a desirable embodiment of the present invention.
Figure 5:
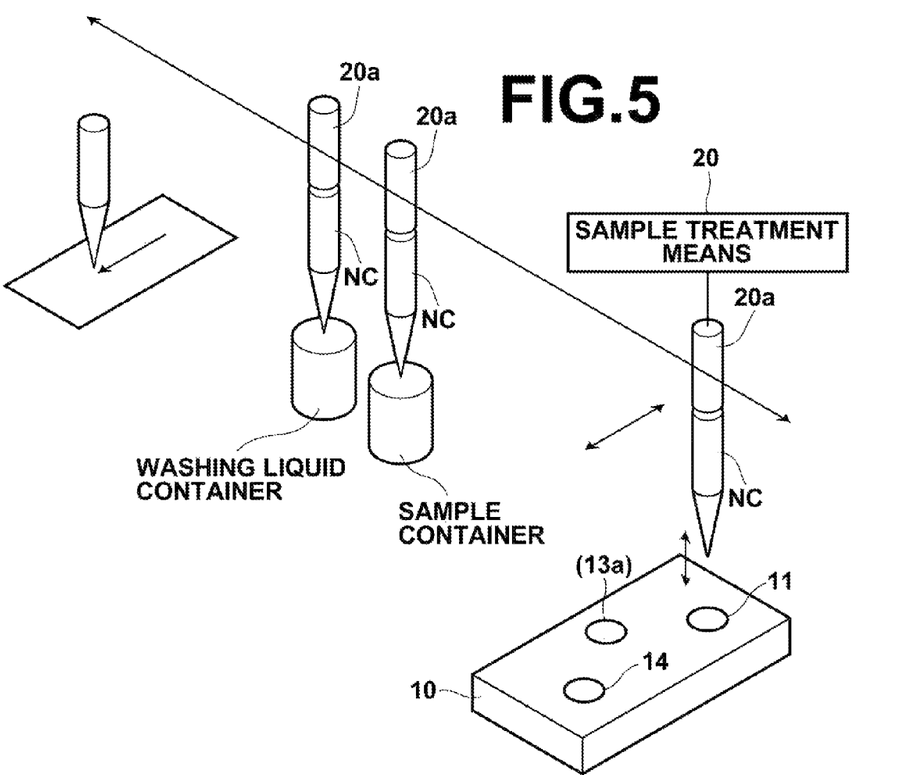
FIG. 5 is a schematic diagram illustrating an example of a sample treatment means illustrated in FIG. 4.

Hereinafter, embodiments of the present invention will be described in detail with reference to drawings. FIG. 1 is a schematic diagram illustrating a developed-color measurement apparatus according to a desirable embodiment of the present invention. FIG. 2 is a schematic diagram illustrating an example of a test strip used in the developed-color measurement apparatus of the present invention. FIG. 3 is a schematic diagram illustrating an example of a test strip used in the developed-color measurement apparatus of the present invention. FIG. 4 is a block diagram illustrating a developed-color measurement apparatus according to a desirable embodiment of the present invention. FIG. 5 is a schematic diagram illustrating an example of a sample treatment means illustrated in FIG. 4.

A developed-color measurement apparatus 1 reads a test strip 10 for detecting an analyte, for example, by using an immunochromatography technique. As illustrated in FIG. 1, the developed-color measurement apparatus 1 includes a case 2, a device insertion opening 3, an information output means 4, and the like. A test strip on which a drop of sample solution has been deposited is inserted to the device insertion opening 3, and a developed color reaction induced on the test strip 10 is optically read out. Further, a readout result is output to the information output means 4. The information output means 4 is an operation panel, for example, composed of a liquid crystal touch panel. A user can input basic setting for measurement through the operation panel.

As illustrated in FIGS. 2 and 3, the test strip 10 is a device for performing qualitative (negative/positive) test about an analyte by using an immunochromatography method, and the analyte (a predetermined antigen) is labeled in a visually recognizable manner. A drop of sample solution obtained by mixing together a sample in which the analyte may be present and a labeled antibody (an antibody labeled with a fluorescent label) that binds to the analyte is deposited on the test strip 10.

Here, the fluorescent label is not particularly limited, but when the fluorescent label is a semiconductor nanoparticle or nanoparticles, high-intensity fluorescence emission is obtainable. Further, when the fluorescent label is the semiconductor nanoparticle or nanoparticles, it is possible to separate the wavelength of excitation light and the wavelength of fluorescence from each other by a great difference. In such structure, it is possible to easily distinguish fluorescence emission and excitation light from each other. Therefore, more accurate judgment of a test result is possible.

The test strip 10 includes an upper case 10A, a lower case 10B, and an insoluble carrier 12. The insoluble carrier 12 is housed in the upper case 10A and the lower case 10B. In the upper case 10A, a through hole 11 for depositing a drop of sample solution on the insoluble carrier 12 from the outside of the test strip 10, a through hole, not illustrated, for depositing a drop of washing liquid on a washing layer 13a, which will be described later, and the like are formed. Meanwhile, the insoluble carrier 12 is fixed to the lower case 10B. Further, an observation window 10Z for observing quantitative or qualitative measurement about the analyte is formed in the lower case 10B. Further, an information storage means 15, such as character information, a bar code and an IC tag, in which information for identifying a sample (a patient's name, or the like), information about time required for reaction, and the like are recorded is provided on the outer surface of the lower case 10B.

The insoluble carrier 12 is made of, for example, cellulose filter paper, glass fibers, and absorbent, such as polyurethane. The deposited drop of sample solution flows in a constant direction by capillary phenomenon. Test area TL and control area CL have been formed on the insoluble carrier 12. In test area TL (a test line), a first antibody having specificity to the analyte (antigen) has been immobilized. When the analyte is present, a conjugate of the first antibody—the analyte—a labeled antibody is formed, and a color is developed in a line shape. Meanwhile, an antigen (or an antibody) for reference that reacts to the labeled antibody has been immobilized in control area CL. When the antigen (or the antibody) for reference reacts with the labeled antibody in the sample solution, a color is developed in a line shape. Therefore, it is possible to judge whether the sample solution has flowed on test area TL and control area CL by checking the color-developed state (fluorescence emission state) of control area CL.

Further, the test strip 10 includes washing layers 13a and 13b that form a flow channel of washing liquid to wash test area TL and control area CL. The washing layers 13a and 13b are provided in such a manner to sandwich test area TL and control area CL therebetween in the vertical direction of FIG. 3 (a direction substantially orthogonal to a flow channel of sample solution). The washing layers 13a and 13b are made of a similar material to the material of the insoluble carrier 12, and the washing liquid flows in an area in which the washing layers 13a and 13b and the insoluble carrier 12 are connected to each other. Therefore, in FIG. 3, the washing liquid flows in the vicinity of test area TL and control area CL including test area TL and control area CL.

When the washing liquid is supplied from the sample treatment means 20 to the washing layer 13a, the washing liquid flows from the washing layer 13a toward the washing layer 13b side by capillary phenomenon. Therefore, the washing liquid flows to test area TL and control area CL present between the washing layers 13a and 13b. Accordingly, a labeled antibody on test area TL and control area CL that has not formed an immune complex is removed.

As illustrated in FIGS. 4 and 5, the developed-color measurement apparatus 1 includes a sample treatment means (a washing liquid supply means) 20, a readout means 21 that detects a fluorescence emission state of a test area, a judgment means 22 that judges, based on a result of detection by the readout means 21, whether an analyte is present in the test strip, a light source 25 that outputs excitation light L, which excites a fluorescent label, and a control means 30 that controls these means. Meanwhile, a judgment means recited in the claims is composed of the readout means 21 and the judgment means 22.

The sample treatment means 20 supplies various kinds of solution necessary in the step of dropping a sample and the step of washing to the test strip 10. Here, the sample treatment means 20 illustrated in FIG. 5 has a function for automatically depositing a drop of sample solution and a drop of washing liquid onto the test strip 10. The test strip 10, a sample container in which a sample is stored, a washing liquid container in which a washing liquid is stored, and plural changeable nozzle chips (sampler chips) NC that are used to dispense various kinds of solution are loaded into the developed-color measurement apparatus 1 in advance.

When start of analysis is instructed, the sample treatment means 20 attaches nozzle chip NC to a nozzle holding unit 20a, and extracts a sample solution from the sample container, and dispenses the sample solution to the test strip 10. In the step of washing, which is performed later, the sample treatment means 20 extracts the washing liquid from the washing liquid container, and dispenses the washing liquid to the test strip 10. Therefore, the sample treatment means 20 functions as a washing liquid supply means.

The readout means 21, illustrated in FIG. 4, reads out the fluorescence emission state of test area TL and the fluorescence emission state of control area CL, as density values, from an observation window 10Z. The readout means 21 is composed of an imaging device, for example, such as a CCD and a CMOS. The readout means 21 may read out grayscale values, as the density values. Alternatively, the readout means 21 may read out values of RGB components, as the density values, or the intensity of a predetermined color (a wavelength component), such as fluorescence, as the density values. Further, the readout means 21 is not limited to the readout means composed of the imaging device. The readout means 21 may be composed of a light receiving element that receives generated reflection light or fluorescence through the observation window 10Z.

The judgment means 22 judges, based on the density value of test area TL and the density value of control area CL that have been read out by the readout means 21, whether an analyte is present. Specifically, the judgment means 22 judges, based on the density value of control area CL, whether the sample solution has been normally developed on the insoluble carrier 12. Further, the judgment means 22 judges, based on whether a difference between the density value of test area TL and the density value of area BR in the vicinity of test area TL has exceeded a predetermined threshold, whether an analyte is present. Further, a result of judgment by the judgment means 22 is output from the information output means 4.

Figure 6:
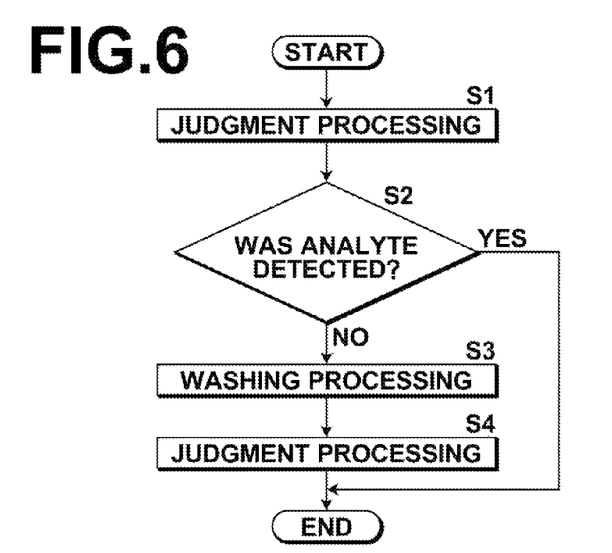
FIG. 6 is a flowchart of a developed-color measurement method according to a desirable embodiment of the present invention.
Figure 7:
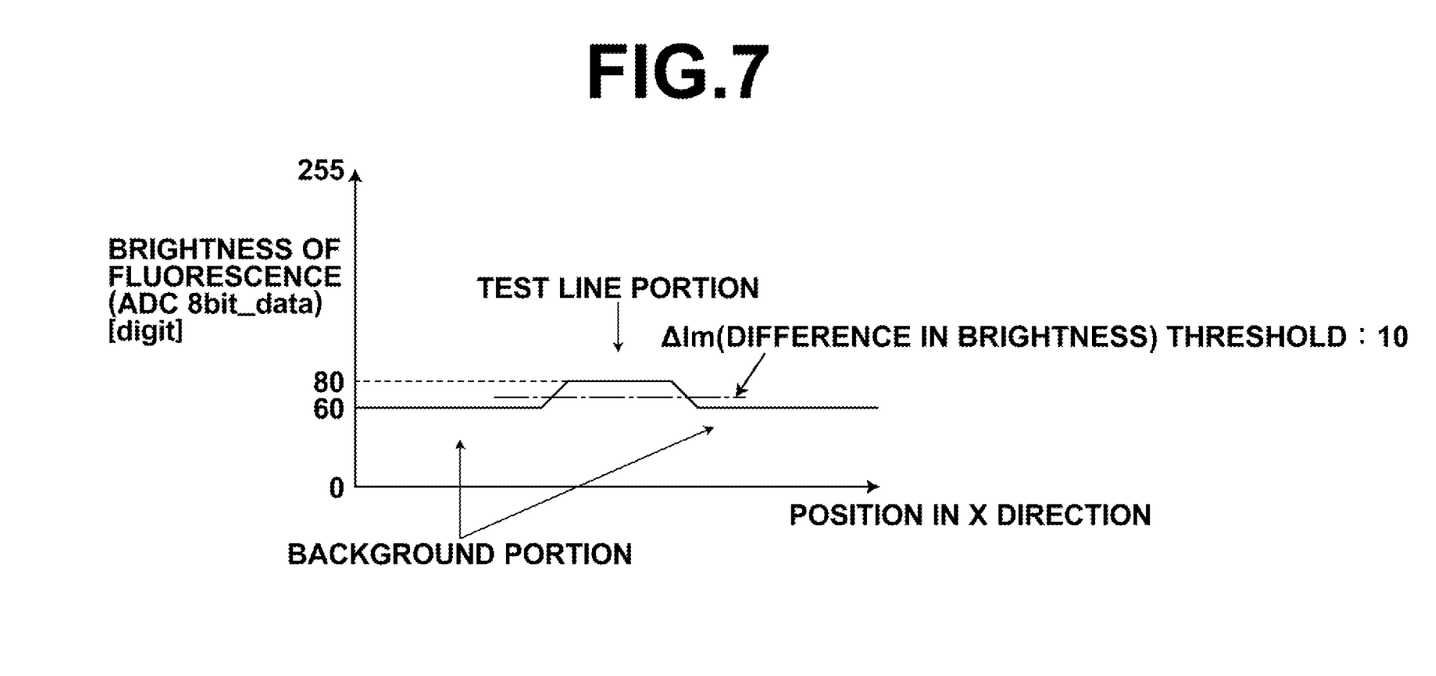
FIG. 7 is a graph illustrating an example of a result of detection of a fluorescence emission state before washing.
Figure 8:
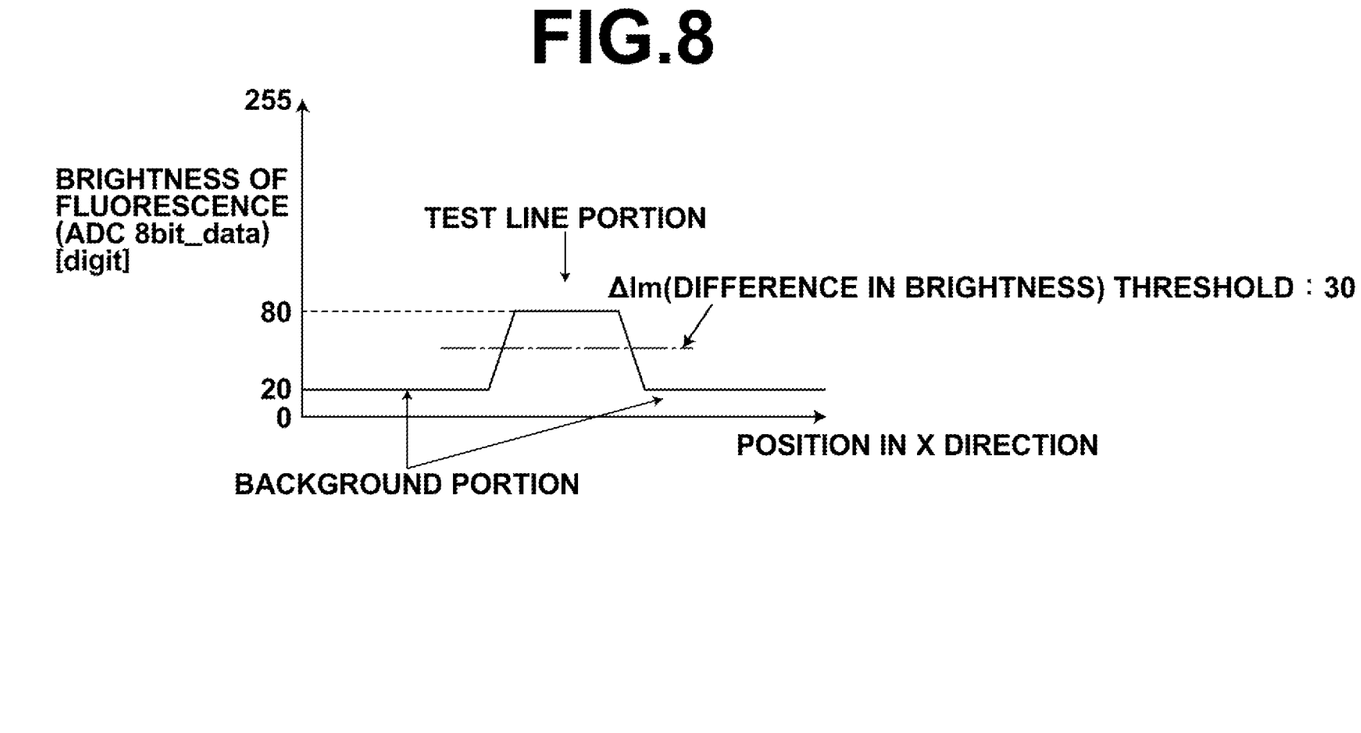
FIG. 8 is a graph illustrating an example of a result of detection of a fluorescence emission state after washing.

Next, a method for judging whether an analyte is present in the developed-color measurement apparatus of the present invention will be described. FIG. 6 is a flowchart of a developed-color measurement method according to a desirable embodiment of the present invention. FIG. 7 is a graph illustrating an example of a result of detection of a fluorescence emission state before washing. FIG. 8 is a graph illustrating an example of a result of detection of a fluorescence emission state after washing. In this processing, the control means 30 controls the sample treatment means (washing liquid supply means) 20, the readout means 21, the judgment means 22, the light source 25 and the like in an integrated manner.

First, the test strip 10, the sample container, and the like are loaded in the developed-color measurement apparatus 1. Then, the sample treatment means 20 deposits a drop of sample solution on the test strip 10.

Judgment as to whether an analyte is present is performed by outputting excitation light L to the vicinity of test area TL and control area CL in this state (step S1). Here, as illustrated in FIG. 7, judgment as to whether the analyte is present is performed based on whether a difference between the density value of test area TL and the density value of area BR in the vicinity of test area TL has exceeded a predetermined threshold (the threshold is 10 in the embodiment of the present invention). Then, if the analyte is detected in step S1, processing ends immediately (step S2).

If the analyte is not detected in step S1, processing changes (step S2), and the washing processing is performed (step S3). A labeled antibody on test area TL and control area CL that has not formed an immune complex is removed in the washing processing.

After then, judgment as to whether the analyte is present is performed again (step S4). Here, when judgment is made in such a manner to judge that the analyte is present in the test strip 10 if a difference between the density value of test area TL and the density value of area BR in the vicinity of test area TL has exceeded a predetermined threshold, as in the embodiment of the present invention, the possibility of erroneous detection is lower as a greater value is set as the threshold. Therefore, the accuracy of detection is improved. At the same time, the possibility of missing detection becomes higher. However, when washing is performed as described above, it is possible to improve an S/N ratio. Therefore, it is possible to improve the accuracy of detection in the judgment processing performed after washing by setting a greater threshold in the judgment processing after washing than the threshold used in the judgment processing before washing.

Here, how much the threshold after washing is greater than the threshold before washing should be appropriately set by taking the configuration of an apparatus, the kind of a fluorescent label, the amount of noise reduced by washing, and the like into consideration. When the threshold after washing is at least about three times as great as the threshold before washing, a desirable effect is achievable.

Therefore, here, the threshold after washing is set three times as great as the threshold before washing (the threshold after washing is 30 in the embodiment of the present invention), as illustrated in FIG. 8. Further, judgment as to whether the analyte is present is performed based on whether a difference between the density value of test area TL and the density value of area BR in the vicinity of test area TL has exceeded the threshold, and processing ends.

As described above, washing is performed only when the analyte has not been detected. Therefore, it is possible to achieve both the reliability of measurement and reduction in time for measurement.

So far, desirable embodiments of the present invention have been described. The present invention is not limited to the aforementioned embodiments. Needless to say, various improvements and modifications are possible without departing from the spirit of the present invention.

What is claimed is:

1. A developed-color measurement apparatus comprising:
    a light source that outputs excitation light that excites a fluorescent label;
    a judgment unit programmed to detect a fluorescence emission state of a
    fluorescent label captured, through an analyte, in a test area of a test strip including an insoluble carrier in which the test area that reacts to the analyte contained in a sample solution is formed, while the excitation light is output to the test area, and perform, based on a result of the detection, judgment as to whether the analyte is present in the sample solution;
        a washing liquid supply unit that supplies a washing liquid for washing the test area and the vicinity of the test area the test strip; and
    a control unit programmed to control the judgment unit and the washing liquid
    supply unit to perform the judgment as to whether the analyte is present in
    the sample solution after the sample solution has been supplied to the test strip but before the test area and the vicinity of the test area are washed, and determine if the analyte is detected and end judgment or determine if the analyte is not detected, wash the test area and the vicinity of the test area and perform the judgment again.

2. The developed-color measurement apparatus, as defined in claim 1, wherein the judgment unit detects a fluorescence emission state of the test area and a fluorescence emission state of the vicinity of the test area, and judges that the analyte is present in the test strip if a difference between a detection value in the test area and a detection value in the vicinity of the test area exceeds a predetermined threshold, and
    wherein a threshold in the judgment after washing is set greater than a threshold in the judgment before washing.

3. The developed-color measurement apparatus, as defined in claim 1, wherein the fluorescent label is a semiconductor nanoparticle.

4. The developed-color measurement apparatus, as defined in claim 2, wherein the fluorescent label is a semiconductor nanoparticle.

5. A developed-color measurement method in a developed-color measurement apparatus comprising:
    outputting excitation light that excites a fluorescent label;
    detecting a fluorescence emission state of a fluorescent label captured, through an analyte, in a test area of a test strip including an insoluble carrier in which the test area that reacts to the analyte contained in a sample solution is formed, while the excitation light is output to the test area,
    performing, based on a result of the detection, judgment as to whether the analyte is present in the sample solution; and if the analyte is detected, ending the judgment, but if the analyte if not detected, washing the test area and the vicinity of the test area and again judging whether the analyte is present or not.

6. The developed-color measurement method, as defined in claim 5, wherein when the judgment unit detects a fluorescence emission state of the test area and a fluorescence emission state of the vicinity of the test area, and judges that the analyte is present in the test strip if a difference between a detection value in the test area and a detection value in the vicinity of the test area exceeds a predetermined threshold, a threshold in the judgment after washing is set greater than a threshold in the judgment before washing.

* * * * *